United States Patent [19]

Steg, Jr. et al.

[11] Patent Number: 5,411,472
[45] Date of Patent: May 2, 1995

[54] LOW TRAUMA BLOOD RECOVERY SYSTEM

[75] Inventors: Robert F. Steg, Jr.; Dean M. Peterson, both of Escondido, Calif.; Dante S. Cusi, Mexico City, Mexico

[73] Assignee: Galen Medical, Inc., Escondido, Calif.

[21] Appl. No.: 922,566

[22] Filed: Jul. 30, 1992

[51] Int. Cl.$^6$ .............................. A61M 1/00
[52] U.S. Cl. ........................ 604/4; 604/257; 604/258; 604/269; 604/902
[58] Field of Search ................. 604/4, 5, 6, 257, 258, 604/266, 269, 902; 433/81, 91, 95, 96

[56] References Cited

U.S. PATENT DOCUMENTS

| | | | |
|---|---|---|---|
| 3,191,600 | 6/1965 | Everett | 128/276 |
| 3,807,401 | 4/1974 | Riggle et al. | 604/269 |
| 4,068,664 | 1/1978 | Sharp et al. | 128/276 |
| 4,321,921 | 3/1982 | Laszczower | 128/276 |
| 4,416,658 | 11/1983 | Numazawa et al. | 604/48 |
| 4,430,073 | 2/1984 | Bemis et al. | 604/48 |
| 4,648,871 | 3/1987 | Jacob | 604/149 |
| 4,666,426 | 5/1987 | Aigner | 604/5 |
| 4,867,738 | 9/1989 | Mintz | 604/4 |
| 4,874,359 | 10/1989 | White et al. | 604/4 |
| 4,892,529 | 1/1990 | Valerio | 604/4 X |
| 5,024,615 | 6/1991 | Buchel | 604/902 X |
| 5,061,180 | 10/1991 | Wiele | 604/902 X |
| 5,163,926 | 11/1992 | Bailey et al. | 604/902 X |

FOREIGN PATENT DOCUMENTS 2117245 10/1983 United Kingdom ............. 604/902
87/04913 8/1987 WIPO .............................. 604/902

Primary Examiner—Sam Rimell
Attorney, Agent, or Firm—Poms, Smith, Lande & Rose

[57] ABSTRACT

Recovery of blood from a wound site (12) during a surgical procedure is accomplished with low blood trauma that enables collection of increased amounts of blood having relatively little structural damage for return to the surgical patient. Blood trauma is decreased by accelerating liquid blood from the wound site to flow at a relatively low velocity with a relatively high negative gauge pressure and accelerating a mixture of blood and foam from the wound site to flow at a relatively high velocity and a relatively low negative gauge pressure. A suction wand is provided in which liquid blood (32) is separated from a mixture of blood and foam (16) at the wound site through the transport of the two separated fluids at the different velocities and negative gauge pressures. The wand includes an outer blood foam tube within which are three resiliently compressed, side-by-side tubes for handling liquid blood, rinse solution and anticoagulant. Low fluidic capacitance filter defoamer modules, having built-in diaphragm operated pumps, receive and filter recovered liquid blood and foam blood for transfer to separate storage bags.

47 Claims, 5 Drawing Sheets

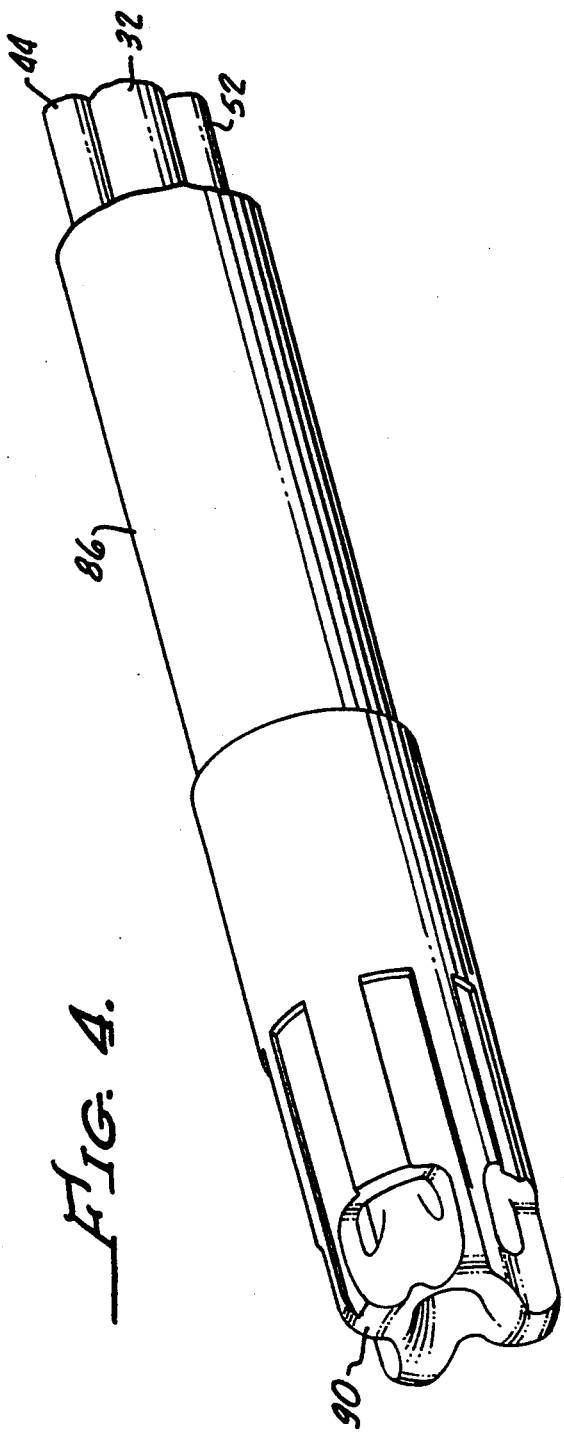
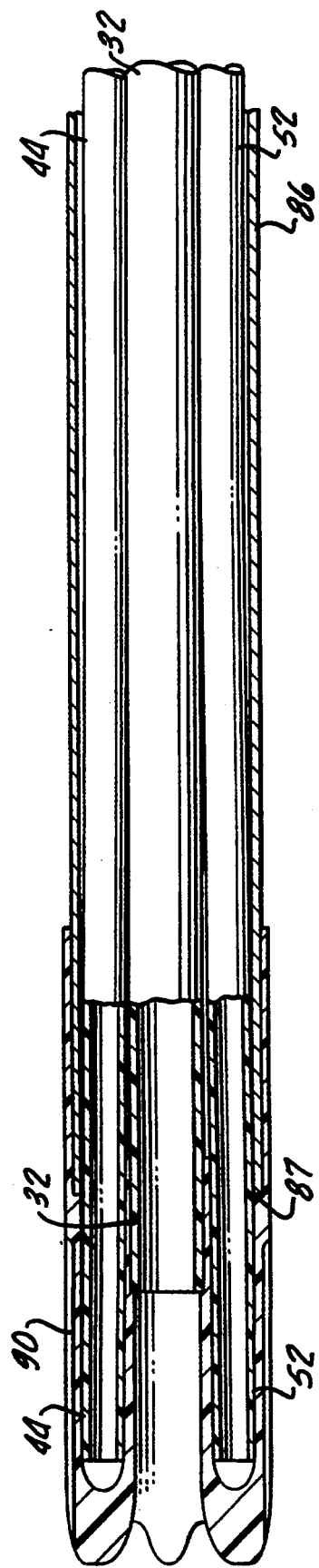

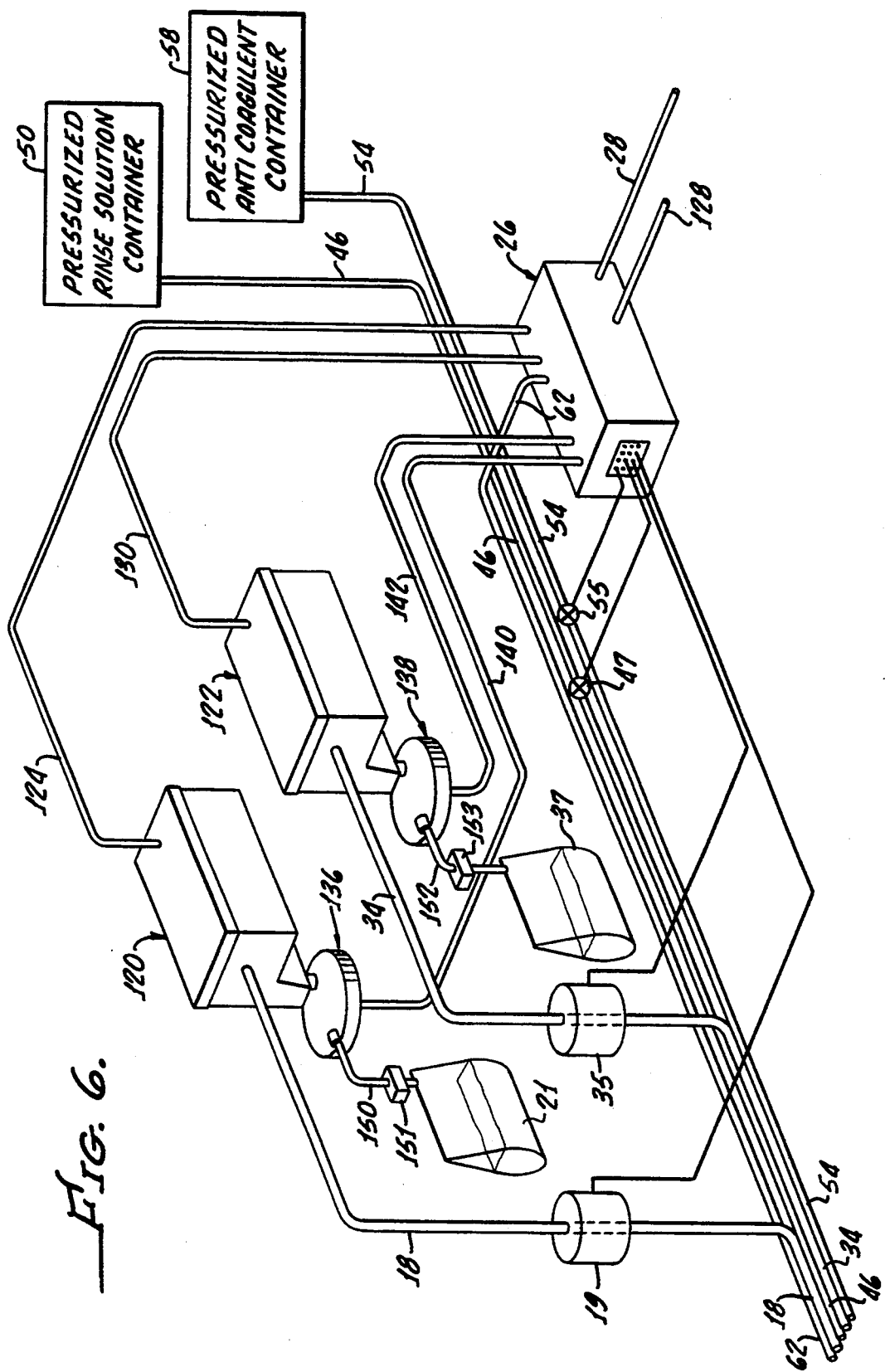

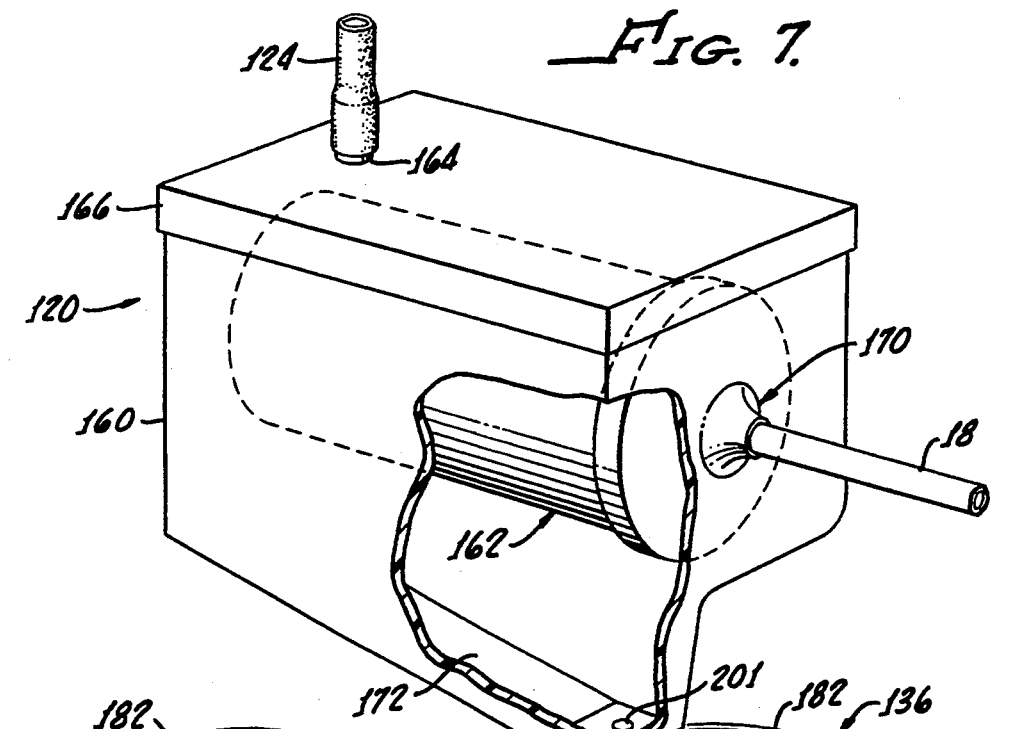
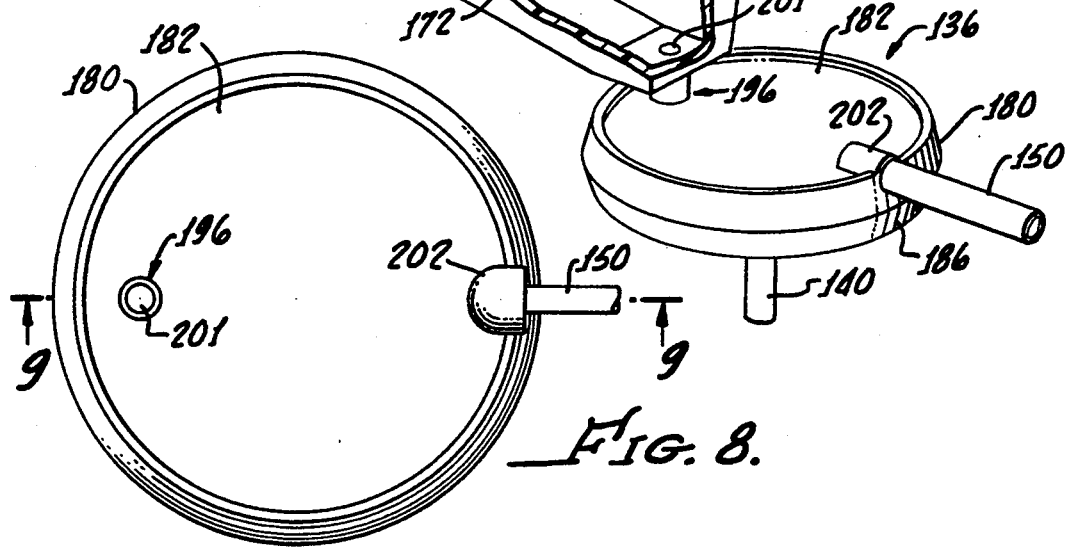
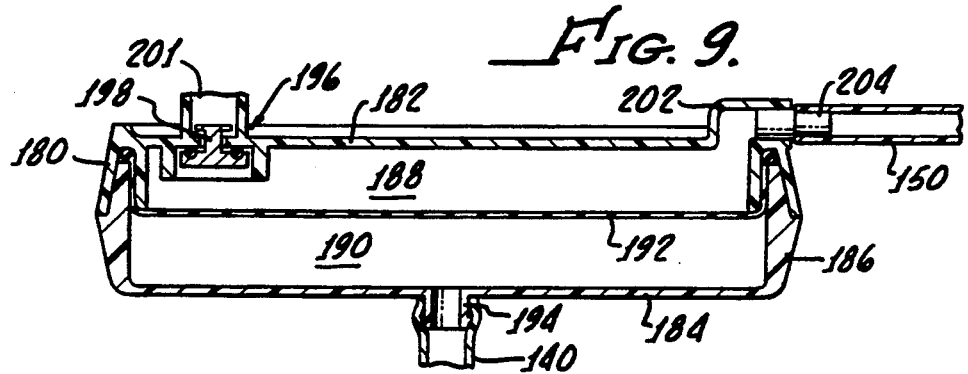

LOW TRAUMA BLOOD RECOVERY SYSTEM

FIELD OF THE INVENTION

The present invention relates to transport of blood with low trauma, and more particularly concerns improved blood recovery wherein blood is transported with decreased mechanical damage.

BACKGROUND OF THE INVENTION

During surgical procedures a suction wand is employed to remove blood from the wound so as to improve visibility to the surgeon and to collect recovered blood for return to the patient. Recovered blood is treated, as by defoaming, filtering and use of a centrifuge to separate damaged blood cells from blood that is to be returned to the patient. The defoaming and filtering apparatus is generally a housing of relatively large internal volume, about 4.2 liters, with part of the housing forming a storage reservoir for the defoamed and filtered blood. To remove blood from the storage reservoir, a separate pump, such as a costly peristaltic pump is employed. Blood is drawn into the filter by applying vacuum to the housing interior. The large filter housing volume acts as a large fluidic capacitance that significantly slows system response to changes in the applied vacuum.

Recovery of blood involves use of mechanical devices which inherently inflict damage on the blood cells because of mechanical handling during the blood recovery. Conventionally recovered blood is cleaned by a centrifuge device, commonly called a cell-saver, to separate intact red blood cells from the lower molecular weight, damaged red cell components as well as other less desirable formed elements of blood.

Various types of blood recovery systems have been employed in the past, generally embodying a suction wand employing a vacuum to suck blood from the wound site through the tip of the wand, which is positioned in the wound site. However, it is well known that all such presently available blood recovery systems cause substantial mechanical blood cell damage, resulting in smaller amounts of recovered blood of relatively lower quality available to be returned to the patient.

Accordingly, it is an object of the present invention to provide blood transport and blood recovery systems that minimize or avoid above mentioned problems.

SUMMARY OF THE INVENTION

In carrying out principles of the present invention in accordance with a preferred embodiment, blood is moved from one location to another with decreased trauma by flowing the blood through a conduit at a significantly decreased velocity. More specifically, liquid blood is caused to flow at a velocity not greater than approximately 1 meter per second. Liquid blood is transported by application of low velocity, relatively high negative gauge pressure gas, causing liquid blood to flow through the conduit. According to another feature of the invention, a suction wand is provided with adjacent or concentric conduits of which a first is arranged to draw liquid blood and a second to draw a foam blood mixture, wherein the liquid blood conduit has applied thereto a relatively high negative gauge pressure throttled by a flow controller to provide a relatively low velocity flow and wherein the foam blood mixture conduit has applied thereto a relatively low negative gauge pressure, but applied via a relatively "open" flow controller, to cause a high velocity conductance of vacuum. According to another feature of the invention, liquid blood is separated from a foam blood mixture at the wound site to enable separate transport and handling of liquid blood and the foam blood mixture.

According to still another feature of the invention, a blood defoamer filter is arranged with a small internal volume to decrease response time to changes in applied negative gauge pressure, and filtered blood is transferred to and stored in a separate, detachable reservoir by means of a vacuum operated pump that forms part of the filter housing.

BRIEF DESCRIPTION OF THE DRAWINGS

FIGS. 4 and 5 show details of the wand nozzle;

FIG. 6 is a simplified perspective view of a pair of defoamer modules, their blood pumps and blood collection reservoirs together with the system control module;

FIG. 7 is a perspective view, with parts broken away, of a defoamer module and pump; and FIGS. 8 and 9 are top and side sectional views, respectively, of a blood pump for one of the defoamer module sections.

DETAILED DESCRIPTION OF A PREFERRED EMBODIMENT

Figure 1:
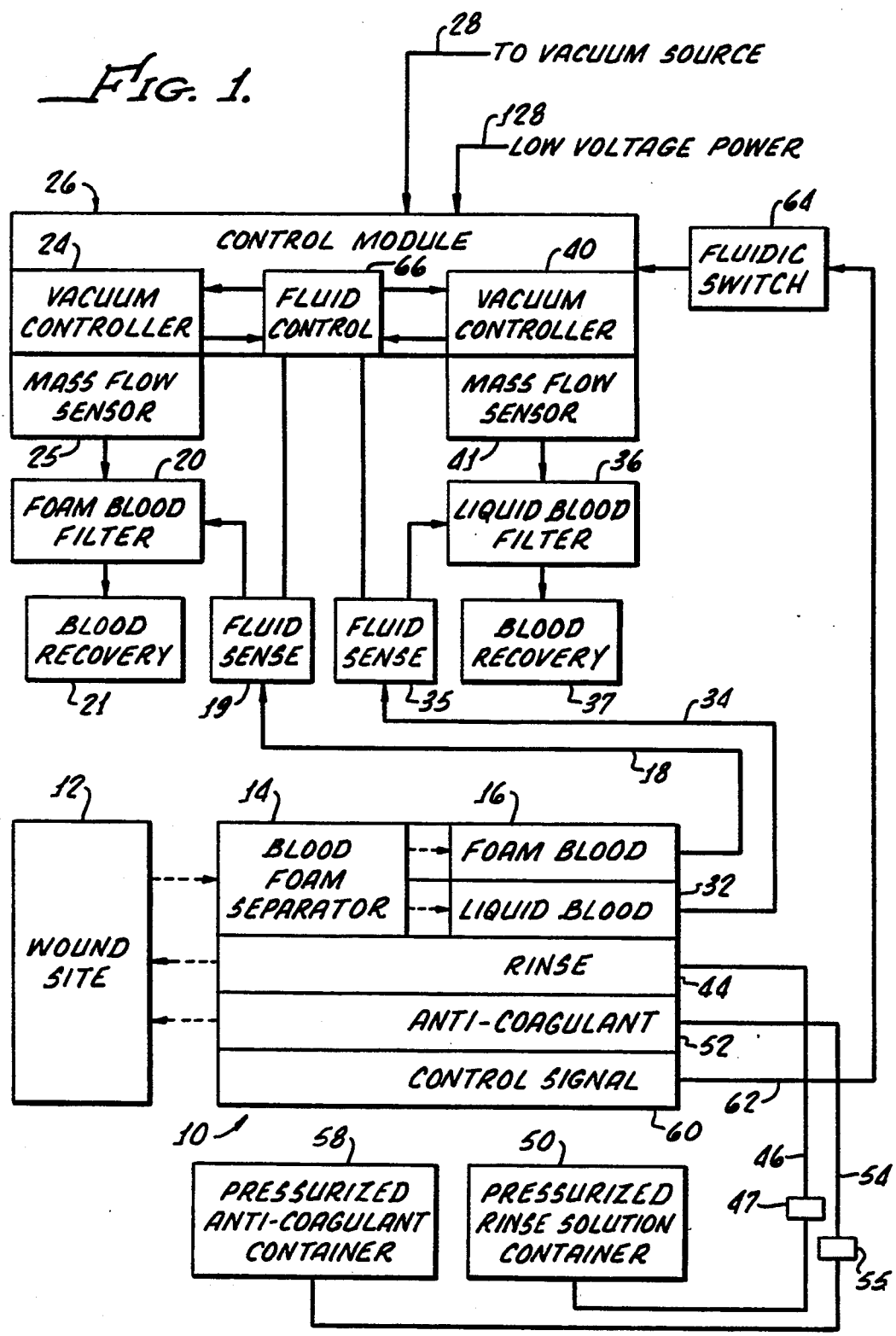
FIG. 1 is a simplified functional block diagram of a system embodying principles of the present invention.

The purpose of the present invention is to maximize blood quality and minimize total blood volume and blood component losses by reducing blood cell degradation that takes place during recovery of blood lost during surgical procedures. Recovery of blood involves use of mechanical devices. The present invention involves a configuration, arrangement and operation of mechanical devices so as to minimize damage that the blood cell suffers because of its handling during blood recovery.

Mechanical blood damage primarily evolves from kinetic energy variations in the form of impact, turbulence, hydraulic friction, sudden velocity changes, pressure changes and similar conditions that produce internal shear in the individual blood cells. Moreover, blood to be recovered tends to foam while it is being handled by mechanical devices. Except for cases in which a gas is used to treat blood in oxygenators, the foam blood is generally produced by the handling devices, and more specifically by the air flow caused by suction in the presence of two phase fluid, liquid and air. A major effect of the presence of a gas in a liquid flow conduit is to increase flow velocity in the conduit. At the relatively low pressures used for blood recovery, flow velocity increases as a direct function of the choice of the volume ratio of gas to liquid. Under normal conditions, this ratio is generally greater than 10:1, even 30:1, with greater velocities employed if the surgeon requires a dry field of view to perform the operation. The increased ratio of gas to liquid, therefore, means that the flow of the blood air mixture may reach velocities that are 10, 30 or even more times greater than the velocity required to move the liquid alone. The increased velocity means increased kinetic energy, which is a primary cause of mechanical blood damage. The problem is greatly magnified by the fact that the kinetic energy involved increases as the square of the flow velocity. The greatly increased kinetic energy is transferred to erythrocytes and thus is a primary source of considerable shear forces that burst the blood cells.

The method and apparatus described herein are arranged to significantly decrease the kinetic energy applied to the liquid blood during blood transport or blood recovery. This is achieved for wound site blood recovery primarily by separating liquid blood from the foam blood mixture and relatively slowly accelerating the liquid blood from substantially zero velocity at the wound site to a low velocity and moving the liquid blood at relatively low velocity and relatively high negative gauge pressure, while separately accelerating the blood foam mixture at a greater rate of acceleration and moving the blood foam mixture at a higher velocity under lower negative gauge pressure.

The relatively high velocities and accelerations required in the foam blood conduit are a function of the surgeon's requirement to have a "dry" operating field of view, but, according to the present invention a major part of the liquid fraction of blood recovered is not subjected to high velocities or acceleration required for clearing the surgeon's field of view. The two otherwise conflicting requirements, high velocity for a "dry" field of view and low velocity for minimum blood damage, are handled separately.

A system embodying these principles is functionally illustrated in FIG. 1, wherein the box generally indicated at 10 represents a suction wand of which specific mechanical configuration is illustrated in FIGS. 2 through 5 and will be described below. The wand is positioned adjacent the wound site, generally indicated at 12, and includes a portion functionally indicated at 14 which separates liquid blood from a foam blood mixture. Foam blood mixture is transported through a foam blood wand conduit 16 via a connecting conduit 18 and through a fluid composition sensor 19 to a cardiotomy reservoir and foam blood filter or defoamer 20. A relatively low negative gauge pressure, high velocity gas (e.g. vacuum) is applied to the foam blood filter 20, and thereby to connecting conduit 18 and foam blood suction wand conduit 16, from a vacuum controller 24 and mass flow sensor 25 forming part of a system control module 26 that exercises control over the entire system. Negative gauge pressure from a vacuum source (not shown) is sustained in the system control module via a line 28. The cardiotomy reservoir has a built-in blood pump that transfers blood to a blood recovering storage bag 21.

A liquid blood wand conduit 32 receives the liquid portion of fluid recovered from the wound site and transports this through a liquid blood connecting conduit 34, through a fluid composition sensor 35 to a second cardiotomy reservoir or blood filter and defoamer 36 to which a high negative gauge pressure low velocity vacuum is applied from a vacuum controller 40 and a mass flow sensor 41 within the system control module 26. This cardiotomy reservoir also has a built-in pump that transfers blood to a blood recovery storage bag 37. Conventional mass flow sensors 25,41 in the control module sense mass flow rate at the output of each vacuum controller and vary flow restricting paths in the sensors in conventional fashion to ensure the relative low velocity of flow in the liquid blood wand conduit 32 and the higher velocity of flow in the foam blood wand conduit 16. Control of mass flow rate to preselected values inherently establishes velocity of flow in the wand conduits (of known, fixed diameter), where no more kinetic energy is transferred to the fluids that were accelerated from the wound site into the wand. The vacuum controllers are further controlled (independently of the mass flow sensors) to establish preselected magnitudes of the negative gauge pressures, at a relatively high value for the low velocity liquid blood flow and at a relatively low value for the high velocity foam blood flow.

The suction wand 10 also includes a rinse application wand conduit 44 which is supplied with a wound rinse solution via a connecting conduit 46 and valve 47 from a pressurized rinse solution container 50. Wand 10 also includes an anticoagulant conduit 52 which receives anticoagulant via a connecting conduit 54 and valve 55 from a pressurized anticoagulant source 58. Mounted to the wand is a manually controlled fluidic switch illustrated as a control signal 60 in FIG. 1 which sends a pneumatic signal via a line 62 to a fluid vacuum switch 64 which may be part of the system control module 26 that controls application of vacuum to the liquid blood and foam blood conduits 32 and 16.

In some applications only negative gauge pressure and velocity of the flow of liquid blood and foam blood need be controlled to pre-established values which maybe varied under manual control. However, for greater system control it may be desirable, but is not necessary, to accomplish further control of the vacuum pressures in response to changes of the density or composition of the fluid flowing in the respective liquid blood and foam blood conduits. For example, it may be desirable to automatically shut off the vacuum to one or the other of liquid and foam blood conduits if it contains only air.

To this end, the system control module may include a fluid density control device 66 that controls the vacuum controllers 24 and 40 to control the negative gauge pressure applied to the foam blood wand conduit 16 and liquid blood wand conduit 32 according to sensed density of the fluid flowing in the corresponding connecting conduits 18,34. Fluid density is sensed by optical sensors 19,35 positioned in connecting conduits 18,34 to send electrical signals to control 66 that indicate composition (density) of fluid in the conduits.

In general, if a relatively small amount of air is detected in the liquid blood conduit by sensor 35, velocity would be caused to be slower. If a relatively large amount of air is detected in the liquid blood conduit, the vacuum application will momentarily stop and then resume. The arrangement would be such as to avoid continuous return of air mixed with blood and yet not miss any opportunity for the liquid return through the liquid blood wand conduit 32 and its connecting conduit 34. Similarly, should an excess amount of air be detected by sensor 19 flowing through the foam blood conduit, vacuum flow would be reduced in the conduit. If only air is present and only air continues to flow in the foam blood conduit, vacuum flow will gradually be reduced until it momentarily stops. Vacuum flow will be ramped up periodically to check for presence of non-air (liquid blood or foam blood) in either blood conduit. If non-air is detected, vacuum flow will continue. If the negative gauge pressure in either conduit is relatively high and there is little or no flow in a given conduit, vacuum will be momentarily shut off to avoid the tendency to pull wound site tissue into the suction wand.

Figure 2:
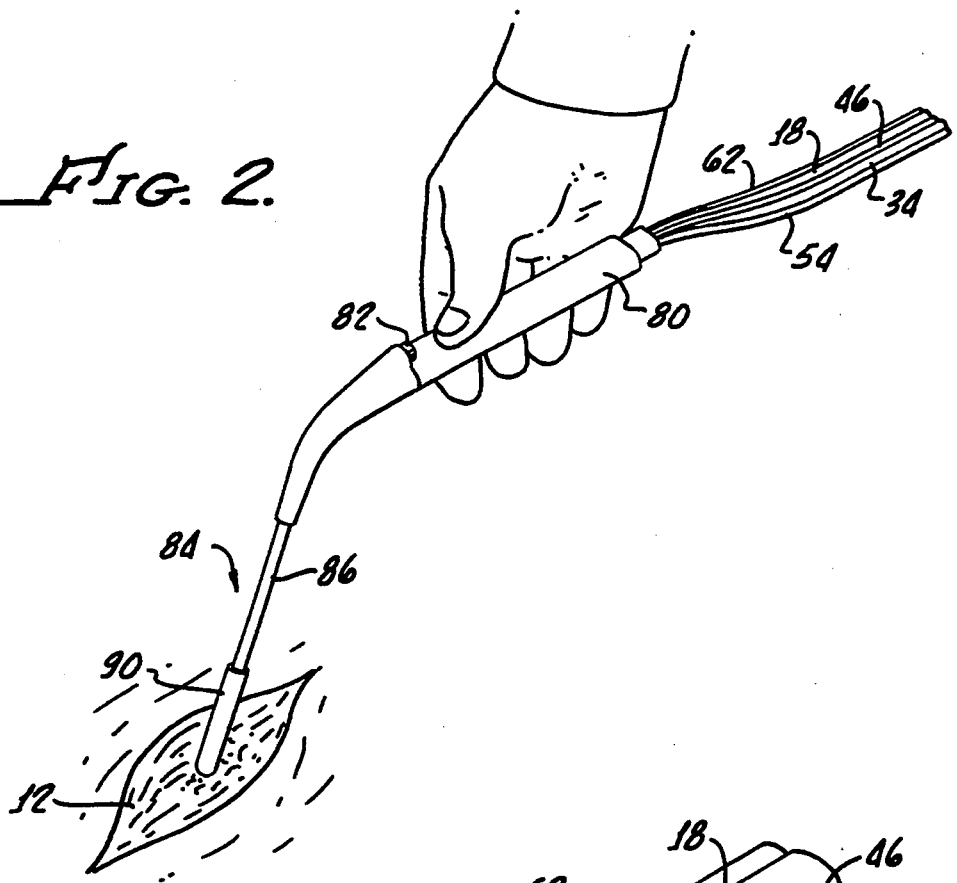
FIGS. 2 and 3 illustrate details of a suction wand structure useful in the practice of the invention.
Figure 3:
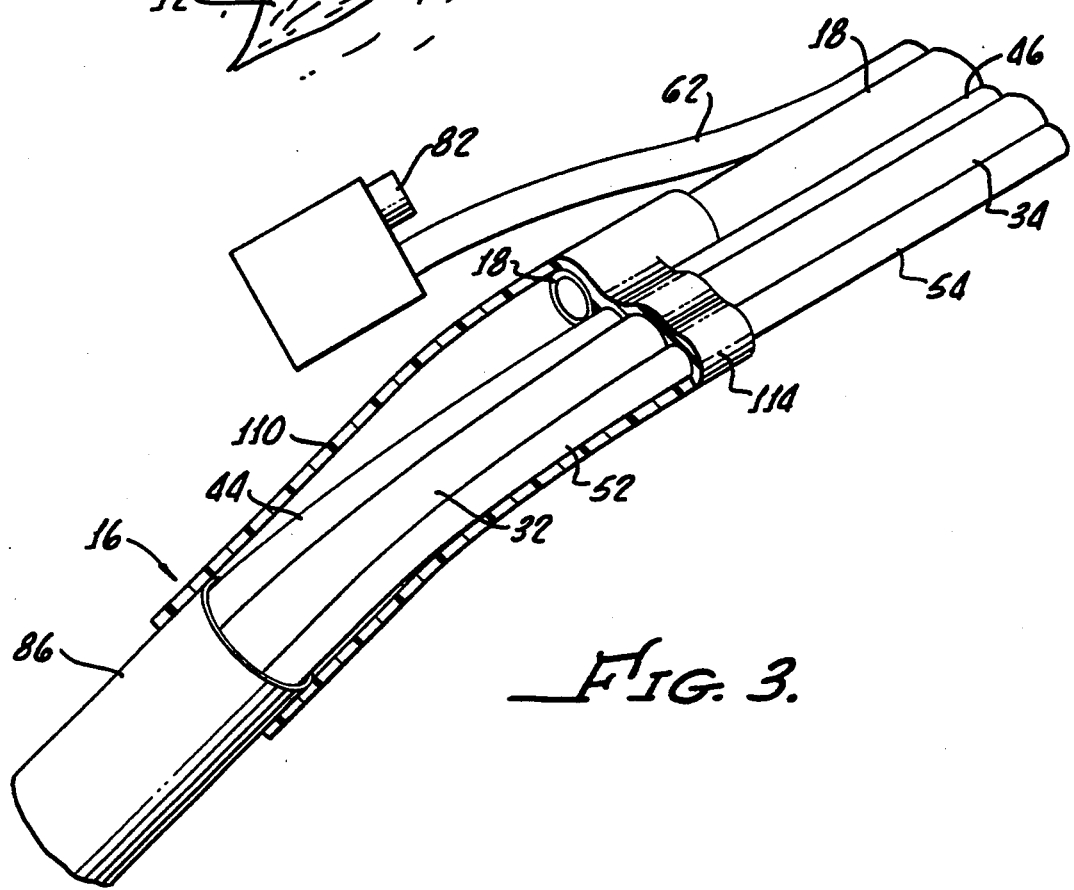

Illustrated in FIGS. 2 through 4 are details of the suction wand and its multiple conduits. The illustrations of FIGS. 3–5 are greatly enlarged. The several conduits of the wand may be arranged in any one of a number of different configurations, such as concentric arrangements, side-by-side arrangements, or some combination thereof. In a presently preferred embodiment the suction wand comprises a wand handle 80 carrying a finger operated controlled fluidic switch 82 for operation of the control signal 60 illustrated in FIG. 1. Conduit sections are termed "wand conduits" within the handle and wand structure, and are termed "connecting conduits" outside of the handle where they connect with the control module and solution containers. Fixedly connected to and extending from the distal (away from the wound site) end of handle 80 are the connecting conduits (18,34,46,54,62). FIGS. 3 and 5 show the wand conduits within the wand. The wand conduits comprise an outer stainless steel enlarged diameter conduit section 86 which receives the foam blood mixture and forms a proximal part of the foam blood wand conduit 16 of FIG. 1. The proximal end of the stainless steel outer conduit 86 is provided with a bail or screen 90 (FIGS. 4 and 5), made of a high strength polymer, having a plurality of openings arranged to restrict the entrance of soft tissue into the suction conduits and to keep blood shear forces and nucleation sites to a minimum. Ends of the rinse and anticoagulant wand conduits 44,52 are received in the end of the bail (FIG. 5).

The liquid blood wand conduit is formed by the inner wand conduit 32 within the outer foam blood conduit section 86 and having a considerably smaller diameter. Liquid blood conduit 32 has an internal diameter of about 3 millimeters and extends 3 to 5 millimeters beyond the end 87 of foam blood mixture conduit section 86 as best seen in FIG. 5. The arrangement is such that the end of the liquid blood conduit 32 may be inserted below the surface of a pool of blood, where such a pool exists, with the end of the foam blood mixture conduit section 86 just touching the blood pool surface. Because of surface tension effects, liquid blood from rivulets of blood at the wound site, tend to elevate along the outside of liquid blood conduit 32 reducing the vacuum flow required to move the fluid into blood foam conduit section 86.

Also confined within the outer foam blood wand conduit section 86 are the rinse conduit 44 and the anticoagulant conduit 52. In a presently contemplated arrangement, the three wand conduits 32, 44 and 52 are formed as a single integral side-by-side extrusion of a resilient plastic and have a total transverse dimension in the direction extending from the rinse conduit 44 to the anticoagulant conduit 52 that is slightly greater, in unstressed condition, than the inner diameter of the outer foam blood mixture wand conduit section 86. The three wand conduits 32, 44 and 52 are transversely compressed when inserted within the outer conduit 86 and, being formed of a resilient plastic, are thereby resiliently secured and mounted to and within the interior of the outer conduit 86.

As can be seen in FIG. 3, foam blood connecting conduit 18 connects with an enlarged crossover transition section 110 of the foam blood wand conduit which in turn connects with wand conduit section 86 so that foam blood flows through conduit sections 86,110. Conduit sections 86 and 110 collectively form the foam blood wand conduit 16. The three wand conduits 32, 44 and 52 enter enlarged transition section 110 that connects the outer expanded diameter wand conduit section 86 to foam blood connecting conduit 18. The three conduits 32, 44 and 52 pass through a crossover arrangement 114 at the rear portion of transition section 110, which enables the three conduits to extend from a position along the exterior of the foam blood connecting conduit 18 to the interior of transition section 110, with a sealed connection that appropriately seals the crossover 114 of transition section 110 to the exteriors of all three conduits 32, 44, and 52.

The control signal connecting conduit 62 extends through the wand handle 80 and connects to the finger controlled fluidic switch 82 having a body portion 83 mounted within the wand handle so as to enable application of negative gauge pressure to the normally open vacuum switch 64 located at the system control module 26. Application of the surgeon's finger to the fluidic switch 82 connects the interior of signal conduit 62 to ambient atmosphere, thereby abruptly reducing the negative gauge pressure in conduit 62 and sending a higher pressure (lower vacuum) signal to the vacuum switch 64. Thus a momentary actuation of the finger controlled fluidic switch 82 provides a momentary pressure pulse to the switch 64. A series of such pressure pulses, either of the same short duration or of varying and mixed long and short durations, may be employed to send a plurality of signals so as, for example, to apply or stop application of rinse or anticoagulant or to otherwise manually control the suction through one or the other of the liquid blood and foam blood mixture conduits.

Moving, in this description, from the wand toward the system control module, the various wand conduits of FIGS. 2 through 4, labeled with the same reference numerals as employed in FIG. 1, are connected to the control module and fluid source containers by the connecting conduits shown in FIGS. 1 and 6. All five connecting conduits 66a,18,46,34 and 54 between the wand and the various devices connected thereto are formed as a single integral extrusion of five side by side tubes.

Illustrated in FIG. 6 is the arrangement of the pair of defoamer and filter modules and their interconnections with the system control module and the separate blood recovery storage. A pair of mutually identical defoamer and filter modules 120,122 is employed, corresponding respectively to the foam blood filter 20 and liquid blood filter 36 of FIG. 1. Foam blood conduit 18 is connected to the inlet of the foam blood defoamer 120, which has negative gauge pressure applied thereto via a conduit 124 from the system control module 26. As previously mentioned, the latter is connected to the hospital vacuum source via a conduit 28. Low voltage electrical power for the electronics of the system control module is applied thereto from a suitable power supply via electrical lines 128. The liquid blood connecting conduit 34 is connected to the second defoamer and filter module 122, which itself is provided with negative gauge pressure via a conduit 130 that is connected to the system control module. Anticoagulant conduit 54 and rinse conduit 46 are connected to the pressurized anticoagulant container 58 and the pressurized rinse solution container 50 via pinch clamps or valves 47,55 that are controlled either manually or by the system control module. Similarly, the control signal conduit 62 is connected to vacuum switch 64 (see FIG. 1) in the system control module.

Instead of employing separate, expensive peristaltic pumps to remove fluid from the defoamer modules (both of which have negative gauge pressure applied to their interiors), a single built-in diaphragm pump 136 for defoamer module 120 and an identical pump 138 for defoamer module 122 are provided. The diaphragm pumps, which may be integral with the defoamer module housings, are fixedly mounted thereto. They are operated via a repetitively modulated negative gauge pressure provided from the control module to the respective pumps via conduits 140 and 142, respectively. The pumps have outputs connected via conduits 150 and 152 and disconnectable aseptic connectors 151,153 to the flexible blood collection bags 21,37 respectively. Because little storage capacity is provided in the filter, separate, detachable storage bags are provided.

The two defoamer and filter modules, one for the liquid blood and one for the foam blood mixture, are identical to each other so that a description of one will suffice to describe both. Details of one, such as the foam blood defoamer module 120, are illustrated in FIG. 7. The defoamer module includes a housing 160 (FIG. 7) in which is mounted a cylindrical horizontal defoamer and filter 162 formed of three or more concentric layers. As an example, the first layer, the inner layer of the three, may be made of a thermoset or woven olefin material coated with antifoam "A". It has a number of longitudinally extending pleats and actually may be formed of several concentric layers. The second layer of the defoamer cylinder 162 is also made of a thermoset or woven olefin material coated with antifoam "A", but is more densely structured than the first layer. The third layer is a concentrically wrapped woven polyester 30 or 40 micron filter material which may, if desirable, be preceded by a pre-filter layer of about 80 to 100 microns. An input vacuum fitting 164 is provided in the airtight removable cover 166 of the housing 160 and connected via vacuum line 124 to the vacuum provided by the vacuum controller 24 of the system control module. Input foam blood mixture is provided via conduit 18 to the interior of the cylindrical defoamer filter cylinder 162 at a centrally located fitting 170 fixed at an end of housing 160. End fitting 170 is softly rounded to provide a gently expanding flow passage for blood entering the module 120, so as to decrease blood deceleration and the concomitant rate of transfer of kinetic energy from the blood. This is particularly important for the liquid blood.

The total internal volume of the filter housing 160 is small, not greater than about 2 liters, and preferably about 1.3 liters. No blood storage volume is provided in this small volume, and, therefore, the attached pump is made a part of the filtered defoamer module to enable the filter and defoamed blood to be continuously removed. The low volume of the interior of the filter housing greatly improves the response time of the system to changes in the negative gauge pressure applied through the filter housing to the liquid and foam blood conduits. The system responds faster to turn on, turn off or changes in magnitude of pressure because the fluidic capacitance of the filter modules is decreased.

The lower portion of the housing 160 is provided with a narrow inclined bottom surface 172 that causes defoamed and filtered blood passing through the several layers of the filter-defoamer to flow by gravity toward one end of the housing into which is built or fixedly secured a circular disc shaped vacuum operated membrane blood pump 136. The blood pump may be integral with the housing 160 of the defoamer module, or if deemed necessary or desirable, the blood pump may be separate from but fixed to the defoamer housing. In either case the pump is a permanent, fixed part of the filter module.

The blood pump comprises a flat disc shaped housing 180 (FIGS. 8 and 9) having an upper wall 182 and a lower wall 184 interconnected by a continuous circular end wall 186. Extending diametrically completely across the housing and dividing the latter into upper and lower mutually sealed pumping and pressure chambers 188 and 190 respectively is a flexible membrane 192 that is flexibly oscillated between the upper and lower housing walls by a repetitively pulsating negative gauge pressure applied to pressure chamber 190 via a fitting 194 in lower wall 184. Fitting 194 is connected to the system control module via the conduit 140. Upper wall 182 of the pump is provided with an inlet fitting 196 under control of a floating check valve 198. Fitting 196 is connected to an outlet fitting 201 in the lowermost portion of the filter-defoamer module housing 160. A pump outlet fitting 202 formed in the side wall of the pump housing is provided with a check valve 204 that connects to blood output conduit 150 to flow blood from the defoamer module 120 to the blood collection bag 21. Vacuum oscillation or pulsation of the pump diaphragm is controlled by the system control module to operate the pump at a relatively low frequency, such as for example about 0.5 cycles per second. Thus the same vacuum source, connected via line 28 to the system control module, provides power to move fluid from the wound site and to transfer blood to the storage bags.

Blood filtered and defoamed by the defoamer module flows to the lowermost portion of the defoamer module housing, but does not collect there because it is continuously removed by the pump. Application of a pulsating negative gauge pressure to the pumping chamber 190 causes oscillation of elastic membrane 192 to alternately open inlet valve 198 and close outlet valve 204, thereby drawing blood from the defoamer module into the pump chamber 188 and then closing the inlet valve and opening the outlet valve to flow blood from chamber 188 to the blood collection bag. The blood collection bag 21, which acts as a storage reservoir, is a simple flexible container, although a rigid storage reservoir may be preferred for some applications.

As mentioned above, one of the unique features of the system described herein is the very low fluidic capacitance of the defoamer and filter modules. Standard blood filter and defoamer modules, holding about 2.6 liters of liquid, have a total internal volume of about 4.2 liters. Each module of the present system, on the other hand, preferably has a total internal volume of only 1.3 liters. This 3.3:1 ratio of prior module volume as compared to volume of the present module permits a much more responsive control system. Because of this enhanced response smaller pressure changes are much more rapidly reflected in the sensing transducers, such as the mass flow meters, than is the case in conventional devices.

The controlled pressures and velocities of the described apparatus operate to minimize kinetic energy transferred to the liquid blood. The apparatus and methods have their primary advantage when there is a pool of liquid blood in the wound site. With the presence of a pool of blood, the extending tip of the liquid blood conduit of the suction wand is placed below the blood surface and there is applied to the liquid blood a relatively high negative gauge pressure that is throttled by the mass flow control device to flow at a relatively low velocity. The velocity that is controlled is that of liquid blood drawn into the end of the small diameter liquid blood wand conduit 32, because it is at this area that the kinetic energy of the blood is increased. For example, the relatively high negative gauge pressure for the liquid blood may be in the range of between −150 and −350 torr, and preferably about −250 torr. The flow rate of the liquid blood is regulated with the mass flow controller so as to cause a liquid flow velocity through the liquid blood wand conduit in the range of between 0.2 and 2.0 meters per second. Preferably, to minimize damage to the liquid blood while maintaining adequate recovery rate, flow velocity of the liquid blood is not more than about 1 meter per second.

Flow velocity is dependent upon the internal diameter of the plastic tubing used for the several conduits and upon the effective cross-sectional area of the nozzle at the suction end of the wand, among other things. In an exemplary system mass flow is measured bout 3 meters upstream from the wand nozzle. The liquid blood tubing in the wand has an internal diameter of 3 millimeters. The kinetic energy of the induced air flow is transferred to the blood almost exclusively at the nozzle in this design. The high velocity flow through the approximately 3 meter length of the entire conduit results in little added kinetic energy. Thus the flow rate values (velocities) stated herein refer to velocities at the nozzle end of the wand conduits. Although the fluid flow paths have different diameters along their length, the diameters are known so that measurement of mass flow at an upstream section is readily used to control velocity at a downstream section adjacent the wand nozzle. As mentioned above, it is important that deceleration of the blood at the defoamer and filter be handed carefully as well.

Flow in the foam blood conduit 16 (FIG. 1) in the suction wand, is under control of a relatively low negative gauge pressure, in the range of between about −80 to −200 torr, and preferably about −150 torr. The flow rate in the foam blood conduit is controlled to be at a considerably higher velocity, preferably at a velocity up to but not more than about 45 meters per second. In a preferred arrangement, the flow velocity of the foam blood mixture and the wand tip is more than about 40 times as great as the flow velocity of the liquid blood at the wand tip. The different combinations of pressure and velocity operate together with the liquid and foam blood conduits at the wand tip operate to separate liquid blood from foam blood mixture. This is accomplished at least in part because the greater negative gauge pressure and lower velocity is more effective in drawing the heavier liquid blood into its conduit, whereas the smaller negative gauge pressure and much higher velocity is more effective in drawing the much lighter foam blood mixture into its conduit. The flow rates are controlled in a conventional manner by use of mass flow controllers, such as Porter Mass Flow Rate Controller 200F, to sense flow rate of the negative gauge pressure source and to limit mass flow rate in accordance with measured mass flow rate.

It may be noted that the foam blood mixture is created primarily by action of the relatively high velocity air flow that is drawn into the foam blood conduit 16 of the suction wand. In order to remove relatively small amounts of thinly flowing or layered blood from the wound site so that the surgeon may see the fine detail of the wound, it is necessary to transfer relatively high amounts of kinetic energy from a high velocity air stream moving over the thinly flowing blood layer to adequately move the blood from the wound site into the foam blood conduit 16. The blood becomes foamy as it is caught in the necessarily excessively fast moving air stream required to keep the wound site clear of blood. This is accomplished by the foam blood wand conduit. As previously mentioned, the pooled liquid blood is not subjected to this high velocity air stream, but rather is subjected to the much lower velocity, higher negative gauge pressure provided to the liquid blood conduit 32 which has its projecting end inserted below the surface of the pooled blood. Thus, significant portions of pooled blood are recovered by the low velocity, low kinetic energy system with greatly decreased blood trauma.

Liquid blood is effectively at rest in the wound site, e.g. at zero velocity. Application of the low velocity relatively high negative gauge pressure to the liquid blood conduit accelerates the liquid blood into the liquid blood conduit from zero velocity to a velocity of flow through the conduit of about one meter per second. Application of the high velocity low negative gauge pressure to the blood foam conduit accelerates some of the blood at a high rate of acceleration, entraining ambient air to create the blood foam mixture and helping to clean the wound site. The blood foam mixture flowing into the blood foam suction conduit rapidly attains its high flow velocity when it enters and flows through the blood foam conduit.

The described system provides a surprising and unexpected decrease in the energy required to extract the foam blood through the foam blood conduit because of the fact that the blood, by means of its capillary action, tends to wick up on the extended external surface of the liquid blood conduit. The blood tends to wick up along the outside of conduit 32, within the outer foam blood conduit 86. This wicking action tends to decrease energy required to extract from the wound site the foam blood mixture that flows through the foam blood conduit.

The described apparatus separates the liquid blood fraction from the two-phase (foam blood fraction), before each of the two fractions is returned in separate conduits at different flow rates and under different negative gauge pressures. This results in significant reduction in the amount of shear stress to which each blood cell is subjected. The system, as described herein, employs high flow capacity, self-priming, blood recovery reservoirs in the form of separate filter and defoamer and modules, each with its own separate (low volume) vacuum compartment and each with its own output pump that is part of the module. The system allows red blood cells and other formed elements of blood to survive much longer than they otherwise would with conventional devices. Highly damaged blood (foam blood mixture) is sequestered independently from liquid blood, permitting return of the foam blood to the patient only in emergencies or after cell washing.

Use of a relatively inexpensive vacuum pump, which is part of the filter and defoamer module, together with the simplified and inexpensive integral extrusion of five side-by-side conduits, the small size of the filter and defoamer modules, and the separate storage bags all cooperate to provide an efficient unit. Not only does the system recover high quantities of blood of better quality, but it is readily produced as an inexpensive throwaway arrangement.

We claim:

1. A low trauma blood recovery system comprising:
   first and second conduits having open ends attached to one another and that terminate closely adjacent to one another and are configured and arranged to be placed at a wound site with both said closely adjacent open ends at the wound site and open to the wound site,
   first means for applying a discrete negative gauge pressure to said first conduit to cause blood to flow through the end of said first conduit at a low velocity, and
   second means for applying a discrete negative gauge pressure to said second conduit to cause flow through the end of said second conduit at a velocity greater than said low velocity.

2. The system of claim 1 wherein said first means comprises means for applying a relatively high negative gauge pressure, low flow rate suction to said first conduit, and wherein said second means comprises means for applying a relatively low negative gauge pressure, high flow rate suction to said second conduit.

3. The apparatus of claim 1 wherein said first conduit lies within said second conduit.

4. The apparatus of claim 1 wherein said second conduit has an end portion adapted to be positioned at a wound site and wherein said first conduit is positioned within said second conduit and has an end portion that projects a small distance beyond the end portion of said second conduit.

5. The apparatus of claim 4 including a third conduit positioned within said second conduit, and means for selectively applying a liquid to said third conduit, said third conduit having an end portion adjacent the end portion of said second conduit.

6. The apparatus of claim 5 wherein said liquid is an anticoagulant.

7. The apparatus of claim 5 wherein said liquid is a wound rinse solution.

8. The apparatus of claim 1 including a wand housing, said first and second conduits being mounted in said wand housing, a signaling fluidic switch on said housing, and a signal conducting conduit coupled with said switch.

9. A low trauma blood recovery system comprising:
   first and second conduits having closely adjacent ends configured and arranged to be placed at a wound site with both said ends at the wound site,
   first means for applying a discrete negative gauge pressure to said first conduit to cause blood to flow through the first conduit at a low velocity,
   second means for applying a discrete negative gauge pressure to said second conduit to cause flow through said second conduit at a velocity greater than said low velocity, and
   a third conduit integrally formed with and extending along said first conduit, said first and third conduits being formed of a resilient material and positioned in a compressed side-by-side relation within said second conduit, the maximum dimension across the total width of said side-by-side first and third conduits in uncompressed relation being greater than the internal diameter of said second conduit, whereby said first and third conduits are resiliently positioned and compressed within said second conduit.

10. A blood recovery system comprising:
    first and second closely adjacent wand conduits having end portions adapted to be placed at a wound site,
    first and second defoamer modules,
    first and second connecting conduits independently connecting said first and second wand conduits with said first and second modules, respectively, and
    means for independently applying negative gauge pressure to each said module, thereby to provide mutually independent negative gauge pressures to said first and second conduits.

11. The recovery system of claim 10 including first and second blood pump means independently connected to said first and second modules respectively for extracting blood from said modules.

12. The apparatus of claim 11 wherein at least one of said blood pump means comprises a housing, a flexible membrane fixed to and extending across said housing and dividing said housing into first and second chambers, means for applying a pulsating vacuum to said first chamber, a blood inlet valve in said second chamber connected with the interior of one of said modules, and a blood output valve in said second chamber.

13. The apparatus of claim 12 wherein said blood pump means are built into said filter module.

14. The apparatus of claim 10 wherein said first conduit comprises a liquid blood conduit and wherein said means for independently applying negative gauge pressure comprises means for applying to said first module a pressure from a negative gauge pressure source and controlling the source to provide low velocity flow through said liquid blood conduit with high negative gauge pressure.

15. The apparatus of claim 14 wherein said second conduit comprises a foam blood conduit and wherein said means for independently applying negative gauge pressure to said second module comprises means for applying pressure from a negative gauge pressure source and controlling the source to provide second velocity flow higher than said low velocity flow with a second negative gauge pressure lower than said high negative gauge pressure.

16. The apparatus of claim 10 wherein said means for independently applying negative gauge pressures to said modules comprises means for applying a negative gauge pressure to said first module to cause blood to flow through said liquid blood conduit at a relatively low velocity of not more than about two meters per second.

17. Blood recovery apparatus comprising:
    a suction wand housing,
    an outer foam blood mixture wand conduit secured to said wand housing having an end portion,
    a plurality of mutually adjacent inner wand conduits within said outer wand conduit and including a liquid blood wand conduit having an end portion projecting slightly beyond the end portion of said outer conduit, and
    a multi-conduit array having individual connecting conduits respectively connected to individual ones of said outer foam blood mixture wand conduit and each of adjacent inner wand conduits within said outer foam blood mixture wand conduit.

18. The apparatus of claim 17 wherein said array includes a foam blood connecting conduit and a liquid blood connecting conduit adjacent and external to said foam blood connecting conduit, said foam blood wand conduit having a crossover transition section connected with said foam blood connecting conduit, said liquid blood connecting conduit extending from a position adjacent said foam blood connecting conduit through said crossover transition section into said outer foam blood wand conduit for connection to said liquid blood wand conduit.

19. The apparatus of claim 17 including first and second filter modules, a first one of said connecting conduits being connected to and between said first module and said outer foam blood mixture wand conduit, a second one of said connecting conduits being connected to and between said second module and said liquid blood wand conduit, a system control module, means for connecting said system control module to a vacuum source, said system control module including a first vacuum controller means for applying a regulated negative gauge pressure to said second filter module to flow liquid blood through said liquid blood wand conduit at a relatively low velocity with a relatively high negative gauge pressure, a second vacuum controller means in said system control module for applying to said first filter module a negative gauge pressure to cause a foam blood mixture to flow through said outer foam blood mixture wand conduit at a relatively high velocity with a relatively low negative gauge pressure.

20. The apparatus of claim 19 including a source of rinse, a source of anticoagulant, said connecting conduits including a rinse connecting conduit and an anticoagulant connecting conduit, said inner wand conduits including an anticoagulant wand conduit and a rinse wand conduit connected to said anticoagulant connecting conduit and to said rinse connecting conduit, respectively.

21. The apparatus of claim 17 including means for applying relatively high negative gauge pressure to one of said connecting conduits so as to cause liquid blood to flow through said liquid blood wand conduit at a velocity of not more than about 1 meter per second, and including means for applying relatively low negative gauge pressure to a second one of said connecting conduits to cause a foam blood mixture to flow through said foam blood mixture wand conduit at a velocity of not less than about 40 liters per second.

22. Blood collection apparatus comprising:
a housing,
a blood defoamer in said housing,
conduit means for introducing blood to be recovered into said housing,
vacuum means for applying a vacuum to said housing to draw blood through said defoamer into said housing,
a storage reservoir connected to the housing, and
pump means mounted to said housing means for transferring blood from said housing to said reservoir, said housing having a total internal volume of not more than two liters for allowing variations of pressure within said housing to be more rapidly responsive to variation of vacuum applied by said vacuum means.

23. The apparatus of claim 22 wherein said reservoir is separate from said housing.

24. The apparatus of claim 23 including means for detachably connecting said reservoir to said housing.

25. The apparatus of claim 23 wherein said reservoir comprises a flexible storage bag, and said means for transferring comprises an aseptic detachable connection.

26. Blood collection apparatus comprising:
a housing,
a blood defoamer and filter in said housing
means for introducing blood to be recovered into said filter,
vacuum means for applying a vacuum to said housing to draw blood through said filter into said housing,
a storage reservoirs, and
means for transferring blood from said housing to said reservoir, said means for transferring comprising a pump body, a flexible diaphragm mounted within said body and extending across the body to divide the body into separate pumping and pressure chambers, said housing having a blood outlet fitting, an inlet valve in said pumping chamber connected to said fitting, an outlet valve in said pumping chamber connected to said storage reservoir, and means for applying a pulsating pressure to said pressure chamber.

27. The apparatus of claim 26 wherein said means for applying a pulsating pressure to said pressure chamber comprises said vacuum means for applying negative gauge pressure to said pressure chamber, and means for varying the pressure applied from said vacuum means to said pressure chamber.

28. A cardiotomy reservoir comprising:
a housing having an output port,
a blood defoamer in the housing,
a blood input port in the housing for flowing blood into the defoamer,
a pump connected to the housing and having an input valve connected to said output port,
means for applying negative gauge pressure to said housing to draw blood into said defoamer, and
means for operating the pump to draw blood from said housing,
said housing having an internal volume of not more than two liters, to improve the response time of internal pressure in the reservoir to changes in negative gauge pressure applied to the housing.

29. A cardiotomy reservoir comprising:
a housing having an output port,
a blood defoamer and filter in the housing,
a blood input port in the housing for flowing blood into the defoamer and filter,
a pump fixed to the housing and having an input valve connected to said output port,
means for applying negative gauge pressure to said housing to draw blood into said defoamer and filter, and
means for operating the pump to draw blood from said housing, said pump comprising a pump housing having an outlet valve, a flexible diaphragm dividing the pump housing into pumping and pressure chambers, said input and outlet valves being in said pumping chamber, and means for applying a pulsating pressure to said diaphragm.

30. A low trauma blood recovery system comprising:
a wand housing,
first and second closely adjacent conduits mounted in said wand housing and having open end portions attached to one another and that terminate closely adjacent to each other adapted to be placed at a wound site to cause each conduit to be independently and directly open to said wound site,
first means for applying a discrete negative gauge pressure to said first conduit to cause blood to flow through the first conduit end portion at a low velocity, second means independent of said first means for applying a discrete negative gauge pressure to said second conduit to cause flow through said second conduit end portion at a velocity independent of said low velocity and greater than said low velocity, a signaling switch on said housing, and signal conducting means connected to said switch and housing for conducting a signal to a location remote from said housing.

31. The system of claim 30 wherein said switch is a fluidic switch.

32. A blood recovery system comprising:
a housing,
a bail
first, second and third closely adjacent conduits mounted in said housing and having open ends in said bail and separately open directly to said wound site, said open ends of said first and second conduits terminating in said bail closely adjacent to one another and being attached to one another by said bail,
first means for applying a discrete negative gauge pressure to said first conduit to cause flow through the first conduit from a wound site,
second means independent of said first means for applying a discrete negative gauge pressure to said second conduit to cause flow through said second conduit from a wound site independent of said flow through said first conduit, and
means for causing flow through said third conduit toward said wound site.

33. Blood recovery apparatus comprising:
a suction wand housing,
an outer wand conduit connected to said housing and having an end portion,
a bail mounted to the end portion of said outer wand conduit,
a first inner wand conduit within said outer wand conduit, said outer wand conduit and said first inner wand conduit having mutually separate open ends mounted in said bail and attached to each other, said open ends terminating in said bail closely adjacent to one another and being configured and arranged to be positioned in mutual proximity within a wound site to enable fluid to be sucked from the wound site at both said open ends,
first and second connecting conduits connected respectively said outer and inner wand conduits, and
a transition section connecting said outer wand conduit with said first connecting conduit.

34. The apparatus of claim 33 wherein said outer wand conduit comprises a foam blood mixture wand conduit and said inner wand conduit comprises a liquid blood wand conduit, said foam blood mixture wand conduit having an end, and said liquid blood wand conduit having an end extending a small distance beyond the end of said foam blood mixture wand conduit.

35. Blood recovery apparatus comprising:
a suction wand housing,
an outer wand conduit connected to said housing,
a first inner wand conduit within said outer wand conduit, said outer wand conduit and said first inner wand conduit having mutually adjacent ends configured and arranged to be positioned in mutual proximity within a wound site to enable fluid to be sucked from the wound site at both said mutually adjacent ends,
first and second connecting conduits connected respectively said outer and inner wand conduits,
a transition section connecting said outer wand conduit with said first connecting conduit, and
a plurality of resilient inner wand conduits within said outer wand conduit, said first inner wand conduit comprising one of said resilient inner wand conduits, said resilient inner wand conduits being transversely compressed against each other and against inner walls of said outer wand conduit thereby resiliently and frictionally securing said inner wand conduits to and within said outer wand conduit.

36. The apparatus of claim 35 including a fluidic finger control switch on said housing, and a fluidic signal conduit connected to said switch.

37. Blood recovery apparatus comprising:
a suction wand housing,
an outer wand conduit connected to said housing,
a first inner wand conduit within said outer wand conduit,
first and second connecting conduits connected respectively said outer and inner wand conduits, and
a transition section connecting said outer wand conduit with said first connecting conduit,
a plurality of resilient inner wand conduits within said outer wand conduit, said first inner wand conduit comprising one of said resilient inner wand conduits, said resilient inner wand conduits being transversely compressed against each other and against inner walls of said outer wand conduit thereby resiliently and frictionally securing said inner wand conduits to and within said outer wand conduit, at least two of said inner resilient wand conduits being formed by a single integral extrusion.

38. Blood recovery apparatus comprising:
a suction wand housing,
an outer wand conduit connected to said housing,
an inner wand conduit within said outer wand conduit,
first and second connecting conduits connected respectively said outer and inner wand conduits,
a transition section connecting said outer wand conduit with said first connecting conduit, said outer wand conduit comprising a foam blood mixture wand conduit and said inner wand conduit comprising a liquid blood wand conduit, said foam blood mixture wand conduit having an end, and said liquid blood wand conduit having an end extending a small distance beyond the end of said foam blood mixture wand conduit, and
a bail fixed to said outer wand conduit and having a bail end, said foam blood mixture wand conduit terminating within said bail at a first distance from said bail end, said liquid blood wand conduit terminating within said bail at a second distance from said bail end that is smaller than said first mentioned distance.

39. Blood recovery apparatus comprising:
a suction wand housing,
an outer wand conduit connected to said housing,
a first inner wand conduit within said outer wand conduit,
first and second connecting conduits connected respectively said outer and inner wand conduits, and a transition section connecting said outer wand conduit with said first connecting conduit, a plurality of resilient inner wand conduits within said outer wand conduit, said first inner wand conduit comprising one of said resilient inner wand conduits, said resilient inner wand conduits being transversely compressed against each other and against inner walls of said outer wand conduit thereby resiliently and frictionally securing said inner wand conduits to and within said outer wand conduit, said outer wand conduit comprising a foam blood mixture wand conduit, said resilient inner wand conduits including a liquid blood wand conduit, a rinse wand conduit and an anticoagulant wand conduit, all compressed against one another within said outer wand conduit.

40. The apparatus of claim 39 wherein said liquid blood wand conduit, said rinse wand conduit and said anticoagulant wand conduit are all formed as a single integral multiple conduit extrusion.

41. The apparatus of claim 40 wherein said connecting conduits comprises a foam blood mixture connecting conduit, a liquid blood connecting conduit, a rinse connecting conduit, and an anticoagulant connecting conduit connecting with respective ones of said wand conduits and all formed of a single integral multiple conduit extrusion.

42. Blood recovery apparatus comprising:
a suction wand housing,
an outer wand conduit connected to said housing,
a first inner wand conduit within said outer wand conduit,
first and second connecting conduits connected respectively said outer and inner wand conduits, and
a transition section connecting said outer wand conduit with said first connecting conduit,
a plurality of resilient inner wand conduits within said outer wand conduit, said first inner wand conduit comprising one of said resilient inner wand conduits, said resilient inner wand conduits being transversely compressed against each other and against inner walls of said outer wand conduit thereby resiliently and frictionally securing said inner wand conduits to and within said outer wand conduit, all of said inner wand conduits being formed as an integral group of side-by-side extruded conduits.

43. The apparatus of claim 42 including means for applying a low velocity high negative pressure to the liquid blood wand conduit and means for applying high velocity low negative pressure to the foam blood mixture wand conduit.

44. The system of claim 1 wherein said low velocity is not greater than about two meters per second.

45. The system of claim 44 wherein the velocity of flow through said second conduit is not greater than about 45 meters per second.

46. The system of claim 45 wherein said first mentioned negative gauge pressure is greater than the negative gauge pressure applied to said second conduit.

47. Blood collection apparatus comprising:
a housing,
a blood defoamer and filter in said housing,
means for introducing blood to be recovered into said filter,
vacuum means for applying a vacuum to said housing to draw blood through said filter into said housing, said housing having a bottom interior surface that forms a relatively narrow inclined passage for flowing defoamed and filtered blood by gravity toward one end of the housing,
said housing having an internal volume of not more than two liters, to improve response time of said internal volume to changes in vacuum applied to said housing,
a membrane blood pump fixedly connected to said housing at said one end thereof, and
a flexible blood storage bag connected to receive blood from said blood pump.

* * * * *